United States Patent

Korsinsky et al.

Patent Number: 5,429,141
Date of Patent: Jul. 4, 1995

[54] AUTOMATICALLY WORN CONDOM

[76] Inventors: Gersh Korsinsky; Eduard Korsinsky, both of 1236 49 St. Apt. #4 B, Brooklyn, N.Y. 11219

[21] Appl. No.: 206,334

[22] Filed: Mar. 7, 1994

[51] Int. Cl.⁶ .............................................. A61F 6/04
[52] U.S. Cl. .................................... 128/844; 128/918; 604/351
[58] Field of Search .............................. 604/349–351; 128/842, 844, 918

[56] References Cited

U.S. PATENT DOCUMENTS

| | | | |
|---|---|---|---|
| 4,862,901 | 9/1989 | Green | 128/844 |
| 4,875,491 | 10/1989 | Parrone | 604/349 |
| 4,966,165 | 10/1990 | Anderson | 128/844 |
| 4,993,433 | 2/1991 | Reddy | 128/844 |
| 5,181,527 | 1/1993 | Dorsey et al. | 128/844 |
| 5,209,241 | 5/1993 | Hardy | 128/844 |

FOREIGN PATENT DOCUMENTS

| | | | |
|---|---|---|---|
| 2649316 | 1/1991 | France | 128/844 |
| 093019704 | 10/1993 | WIPO | 128/844 |

Primary Examiner—Randall L. Green
Assistant Examiner—Rob Clarke

[57] ABSTRACT

A sheath that one wears on a penis automatically by pushing inside or in to the sheath suitable for sexual intercourse with a condom. A portion of the condom is capable of being held within the genital of a woman prior to the insertion of a penis into the condom.

1 Claim, 3 Drawing Sheets

AUTOMATICALLY WORN CONDOM

FIELD OF THE INVENTION

The present invention is related to a safe sex device and more specifically to a condom device.

BACKGROUND OF THE INVENTION

The disadvantage of the known male condoms is the unavoidable disruption of applying them, though it may be that people are well advised to refrain from sexual encounters whose magic and charm are so fragile and evanescent that they can be dispelled by applying a condom.

The male condom wearing problem including the unavoidable disruption in applying them offers no guaranty of safe sex from diseases, such as herpes, syphilis or AIDS. Therefore it appears that women have developed there own female condom.

The female condom developed is not pretty: it looks like a soft loose-fitting sheath with two flexible rings. One ring anchors the device at the sheath's closed end, the other hangs outside of the vagina.

Sexual intercourse with a female condom is not pleasurable. The only advantages of the female condoms are that the women can be sexy and free. They can be relatively safe from sexually transmitted diseases.

A drawback of the known condoms is that they tend to reduce the pleasurable feelings of sexual intercourse. However the known condoms will not solve the modern problems of protected sex to reduce the incidence of diseases, such as herpes or syphilis or AIDS and unintended pregnancies, particularly by teenagers.

OBJECTS OF THE INVENTION

It is an object of the present invention to provide a quick and comfortable wearing of a condom on the male's penis.

It is another object of the present invention to provide a wearing of a condom on a male's penis by access to the female;s genitals during sexual intercourse.

Yet another object of the present invention is to provide a female used condom with qualities and advantages of men's condom.

Yet another object of the present invention to provide a female used condom worn on a male's penis during the processes of sexual intercourse.

A further object of the present invention is to provide an intentional pre-intercoursing wearing of a condom on a male's penis.

A further object of the present invention is to provide a condom which eliminates the known unavoidable disruption in applying known condoms, though it may be that people are well advised to refrain from sexual encounters whose magic and charm are so fragile and evanescent that they can be dispelled by applying a condom.

Still another object of the present invention is to provide for the elimination of the comedy of manners over who wears the condom as a testing ground of chivalry and it's merits.

Another object of the present invention is to provide a female with their own condom for comfortable use on a male's penis during sexual intercourse operations.

A still further object of the present invention is to provide a condom which is attractive for female, men and gay people which is comfortable during sexual intercourse, while hip enough to avoid the psychic damage these nascent days of the so-called sexual revolution that once seemed so profligate and bawdy, seem quaint and innocent now. There was no fear of disease and people didn't have to get pregnant.

SUMMARY OF THE INVENTION

The present invention is directed to providing a self-worn condom on the male's penis by access of the male's penis into the female genitals during sexual intercourse.

The invention solves the wearing problems of the male condom on a man's penis during sexual intercourse process without the intentional, specialized operation to wear a condom before sexual intercourse. The device is worn on a male's penis during sexual intercourse.

The device comprises a men's quality condom and a part for self wearing or transfer of the condom during the access of the penis to the female genitals during sexual intercourse.

The folded condom is held or worn by the female genitals or by a belt or by female underwear or stuck to the female body.

The condom is suitable for comfortable sexual intercourse between sexually active people.

DETAILED DESCRIPTIONS OF PREFERRED EMBODIMENTS

Figure 1:
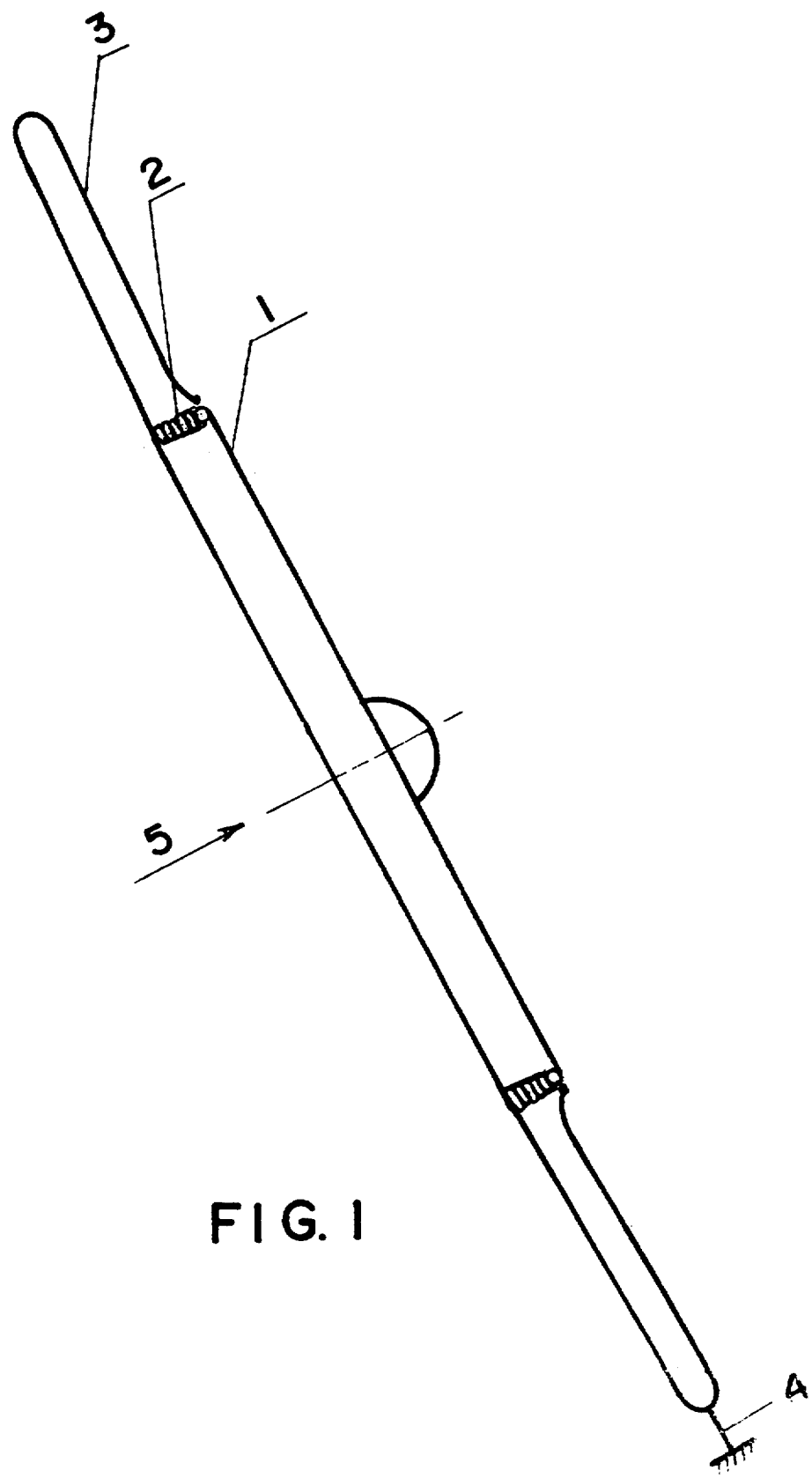
FIG. 1 is a view of the basic principles of an automatically worn condom.

FIG. 1 shows the basic principles for designing a condom device according to one embodiment of the invention. The part 2 of the condom is folded or bent around ring 3 and ring holder 4 in a bellows like an accordion fashion. The condom part 1 will pull or stretch out the condom part 2 causing the condom to be worn on a man's penis as the penis is pushed in direction 5. The ring 1 can be held by a hand.

Figure 2:
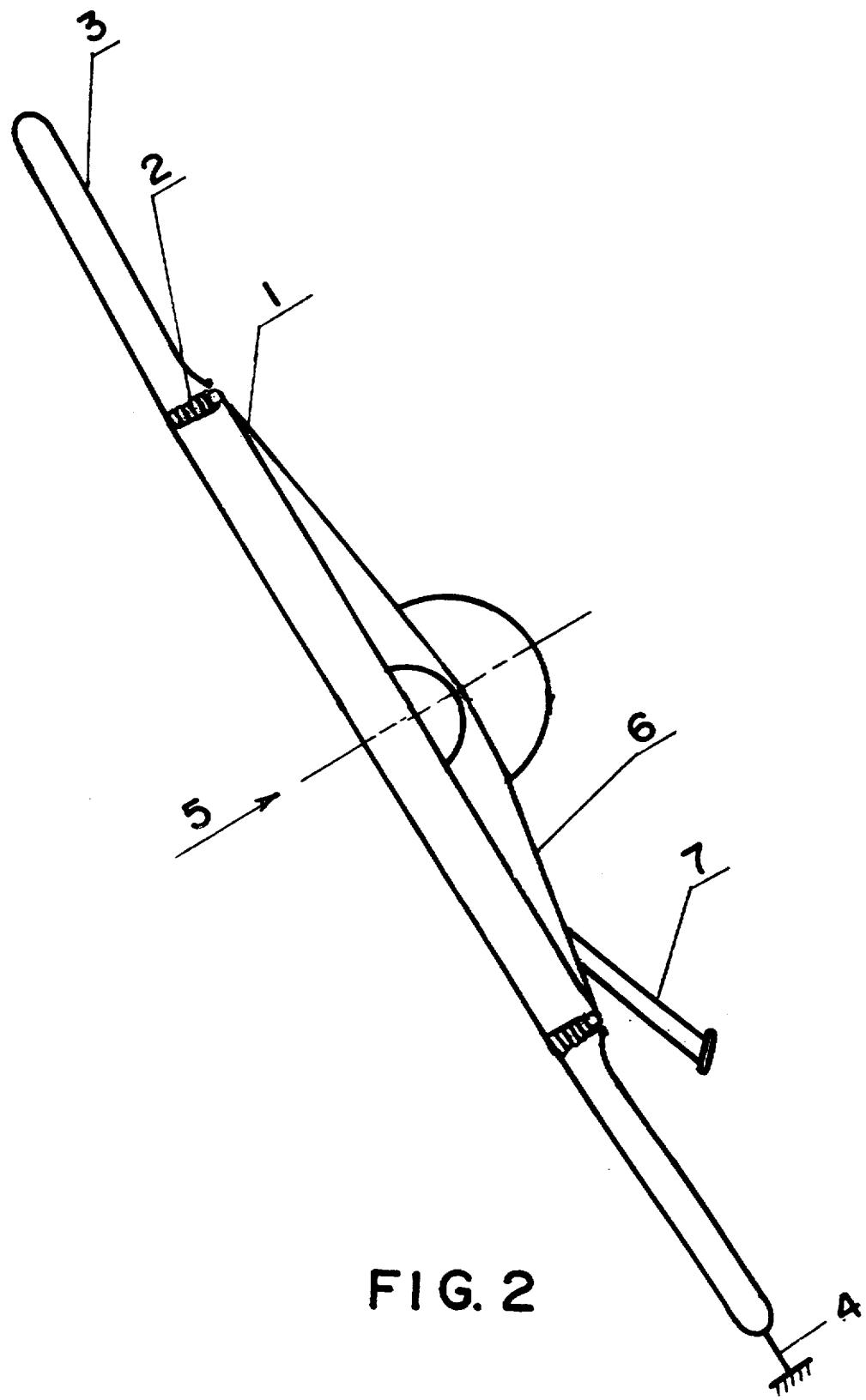
FIG. 2 is a view of the principles of a condom held by an air membrane.

FIG. 2 shows the basic principles for designing a holding (4) of the condom by an air membrane. The membrane (6) will be air filled by valve (7) and will be inserted or put in a female's genitals for holding. The man's penis will tear or rupture the membrane and sill pull or stretch out the condom part (2) thereupon the condom becomes worn on the penis.

Figure 3:
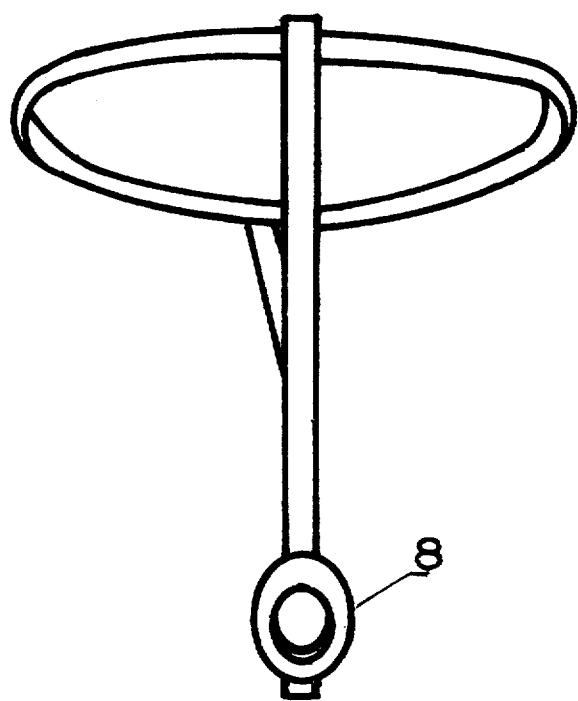
FIG. 3 is a view of the principles of a condom worn by a belt or underwear.

FIG. 3 shows the basic principles for designing a condom worn on a belt or on underwear. Unit (8) is a belt or underwear. Unit (9) is a folded condom held by unit (8).

We claim:

1. An automatically worn condom device comprising:
    a condom holding ring capable of holding the condom folded in a manner like the bellows of an accordion;
    a condom having a closed end and an opposite open end portion;
    the opposite open end portion is held in a bellows like, accordion manner about the condom holding ring prior to insertion of a penis into the condom;
    the closed end of the condom being disposed in the center portion of the condom holding ring,
    and means for holding at least the closed end portion of the condom by the genitals of a female such that when the penis is inserted into the held portion of the condom the bellows like portion of the condom is worn on the penis as the condom is stretched by the penis.

* * * * *